United States Patent [19]

Malz, Jr. et al.

[11] Patent Number: 4,605,743

[45] Date of Patent: Aug. 12, 1986

[54] PROCESS FOR THE PRODUCTION OF 2,2,6,6-TETRAALKYL-4-PIPERIDYLAMINES

[75] Inventors: Russell E. Malz, Jr., Naugatuck; Harold Greenfield, Watertown, both of Conn.

[73] Assignee: Uniroyal Chemical Company, Inc., Middlebury, Conn.

[21] Appl. No.: 723,770

[22] Filed: Apr. 16, 1985

[51] Int. Cl.$^4$ .................. C07D 401/12; C07D 401/14
[52] U.S. Cl. .................................. 546/186; 546/189; 546/191; 546/223; 546/244
[58] Field of Search ............... 546/186, 189, 191, 223, 546/244

[56] References Cited

U.S. PATENT DOCUMENTS

| | | | |
|---|---|---|---|
| 3,480,635 | 11/1969 | Altwicker | 546/191 |
| 3,684,765 | 8/1972 | Matsui et al. | 546/186 |
| 3,734,883 | 5/1973 | Holt | 546/186 |
| 3,853,890 | 12/1974 | Holt | 546/186 |
| 4,046,736 | 9/1977 | Hardy | 546/186 |
| 4,104,248 | 8/1978 | Cantatore | 546/186 |
| 4,191,683 | 3/1980 | Brunetti et al. | 546/189 |
| 4,293,466 | 10/1981 | Di Battista et al. | 546/186 |
| 4,326,063 | 4/1982 | Son | 546/186 |
| 4,415,688 | 11/1983 | Minagawa et al. | 546/186 |

FOREIGN PATENT DOCUMENTS 3007996  9/1981  Fed. Rep. of Germany ...... 546/186

*Primary Examiner*—Robert T. Bond
*Attorney, Agent, or Firm*—William E. Dickheiser

[57] ABSTRACT

2,2,6,6-tetraalkyl-4-piperidylamines are produced by reacting an amine with a 2,2,6,6-tetraalkyl-4-piperidone in the presence of a palladium catalyst.

14 Claims, No Drawings

PROCESS FOR THE PRODUCTION OF 2,2,6,6-TETRAALKYL-4-PIPERIDYLAMINES

FIELD OF THE INVENTION

This invention is directed to an improved process for the production of 2,2,6,6-tetraalkyl-4-piperidylamines, which process involves the use of a palladium catalyst.

BACKGROUND OF THE INVENTION

The use of 2,2,6,6-tetraalkyl-4-piperidylamines, such as N,N'-bis(2,2,6,6-tetramethyl-4-piperidyl)hexamethylenediamine, as ultraviolet stabilizers for polymeric materials is well known in the art. In the past, the production of these compounds has generally involved the use of a platinum catalyst in an aliphatic alcohol solvent.

Thus, U.S. Pat. No. 4,104,248 issued to G. Cantatore shows the production of various N,N'-bis(2,2,6,6-tetramethyl-4-piperidyl)amines employing a platinum on carbon catalyst and utilizing methanol as a reaction medium. Similarly, U.S. Pat. No. 4,326,063 issued to P. N. Son discloses a process for producing 2,2,6,6-tetraalkyl-4-piperidylaminocycloalkyl compounds utilizing a platinum catalyst and a polar organic solvent, such as an aliphatic (lower alkyl) alcohol, while Minagawa et al in U.S. Pat. No. 4,415,688 show the production of certain 2,2,6,6-tetraalkylpiperidylamine compounds employing a platinum/carbon catalyst and methanol as the solvent. In the same vein, U.S. Pat. No. 4,293,466 to Di Battista et al shows the production of N,N'-4-piperidyl-tetraalkyl-substituted alkylene compounds in the presence of a hydrogenation catalyst such as platinum.

However, as is shown in Table I below, the yield of product when a platinum catalyst is employed in a low pressure (100–200 psig) process is relatively low. While the use of higher pressures (e.g., of 600–800 psig) will increase product yield somewhat, as is indicated in Table II below, such high pressure platinum-catalyzed processes will also result in the production of a relatively substantial amount of unrecyclable byproducts (such as 2,2,6,6-tetramethyl-4-piperidinol and the like).

An alternative approach is disclosed in German Offenlegungschrift No. 3,007,996, wherein a Raney nickel or cobalt catalyst is employed in an inert organic solvent to produce polyalkylpiperidylamines. The stated benefit of this process is that low hydrogen pressures of between 5 and 30 bar (between about 72.5 and 435 psi) may be employed. It is noteworthy that the Examples of this publication indicate that at pressures of 20 bar (about 290 psi) the yields of product ranged from 82–93 percent.

From the above, it is apparent that it would be desirable to possess a process for the production of 2,2,6,6-tetraalkyl-4-piperidylamines in increased yields. Moreover, it would be desirable to possess a process for preparing such piperidylamines which would result in reduced amounts of unrecyclable byproducts, such as piperidinols, being produced.

Accordingly, it is an obJect of this invention to provide a process for the production of 2,2,6,6-tetraalkyl-4-piperidylamines which process would provide increased yields.

It is a further object of this invention to provide a process for the production of 2,2,6,6-tetraalkyl-4-piperidylamines which process results in the production of reduced amounts of unrecyclable byproducts.

The above and additional objects will become more apparent from the following description and Examples.

DESCRIPTION OF THE INVENTION

The present invention is directed to a process for producing compounds of the formula:

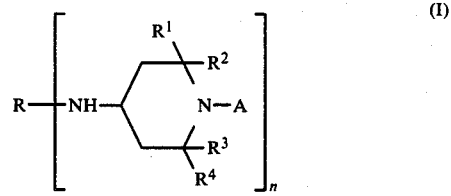

wherein:
R is $C_1$–$C_{18}$ alkyl, $C_5$–$C_6$ cycloalkyl or $C_7$–$C_9$ aralkyl;
$R^1$, $R^2$, $R^3$ and $R^4$ are the same or different and are $C_1$–$C_8$ alkyl;
A is hydrogen, hydroxy, $C_1$–$C_8$ alkoxy, $C_1$–$C_8$ alkyl, $C_2$–$C_{10}$ alkylcarbonyl or arylcarbonyl: and
n is 1, 2, 3 or 4;
with the proviso that when n is 2, 3, or 4, the $R^1$, $R^2$, $R^3$, $R^4$ and A substituents of the pyridine rings may each independently be different members within the scope of their definitions; which process comprises reacting an amine of the formula $R(NH_2)_n$, wherein R and n are as defined above, with at least one 2,2,6,6-tetraalkyl-4-piperidone of the formula:

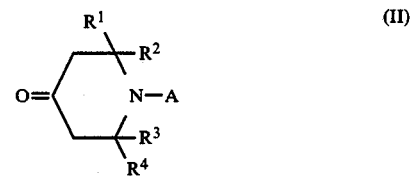

wherein A, $R^1$, $R^2$, $R^3$ and $R^4$ are as defined above; in the presence of a palladium catalyst employing a reaction medium selected from the group consisting of water, $C_1$–$C_{10}$ aliphatic alcohols, $C_2$–$C_6$ aliphatic glycols and mixtures thereof.

As is employed herein, terms such as "2,2,6,6-tetraalkyl-4-piperidylamine" are intended to encompass compounds having substituents bonded to the piperidinyl nitrogen (i.e., "A" substituents).

Moreover, it is to be noted that when n in formula I above is 2, 3, or 4, the $R^1$, $R^2$, $R^3$, $R^4$ and A substituents of the piperidine rings may each independently be different members within the scope of their definitions. Thus, when 2 or more piperidinyl rings are pendent from the resultant compound, the substituents off each of the rings may be different. For example, if n is two, A may be both hydrogen and hydroxyl—i.e., the compound is both 2,2,6,6-tetraalkyl-4-piperidinylamino and 1-hydroxy-2,2,6,6-tetraalkyl-4-piperidinylamino substituted.

Illustrative of the amines which may be employed are aliphatic mono-, di-, tri- and tetramino alkyl amines such as methylamine, butylamine, dodecylamine, octadecylamine, triethylenediamine, tetraethylenediamine, hexamethylenediamine, dipropylenetriamine, diethylenetriamine, 1,2,6-triaminohexane and the like; arylamines such as aniline, phenylenediamine and the like; and aralkylamines such as benzylamine and the like.

Preferred amines are hexamethylenediamine and tetramethylenediamine.

Suitable 4-piperidones which can be used in the process of this invention include 2,2,6,6-tetramethyl-4-piperidone; 1,2,2,6,6-pentamethyl-4-piperidone; 1-ethyl-2,2,6,6-tetramethyl-4-piperidone: 1-n-octyl-2,2,6,6-tetramethyl-4-piperidone; 2,6-diethyl-2,6-dimethyl-4-piperidone; 2-isobutyl-2,6,6-trimethyl-4-piperidone; 1-acetyl-2,2,6,6-tetramethyl-4-piperidone: 1-benzoyl-2,2,6,6-tetramethyl-4-piperidone; 1-hydroxy-2,2,6,6-tetramethyl-4-piperidone; 1-methoxy-2,2,6,6-tetramethyl-4-piperidone; and the like. The preferred 4-piperidone is 2,2,6,6-tetramethyl-4-piperidone.

Many of such suitable 4-piperidones are known compounds. The preparations of many of them can be found in the literature. For example, Francis, J. Chem. Soc., 2897 (1927) discloses a process for the preparation of triacetoneamine, another name for 2,2,6,6-tetramethyl-4-piperidone (where A is hydrogen); Biel & Robertson, U.S. Pat. No. 3,364,220, Example 9, show the preparation of 1,2,2,6,6-pentamethyl-4-piperidone (where A is methyl); Rozantsev and Golubev, Chem. Abs. 65, 10559 (1966), show the preparation of 1-hydroxy-2,2,6,6-tetramethyl-4-piperidone (where A is hydroxy): and Holt, U.S. Pat. No. 3,734,883, column 2 lines 1–18, show the preparation of these compounds where A is methyl. Other compounds within the scope of formula (II) can be prepared similarly.

The palladium catalyst may be employed in the form of a bulk metal or metal oxide. Preferably such catalyst is supported on a suitable carrier such as carbon or aluminum. Sulfided forms of the catalyst may also be employed.

Suitable reaction media include water, $C_1$–$C_{10}$ aliphatic alcohols, $C_2$–$C_6$ aliphatic glycols and mixtures thereof. Preferred reaction media are water, methanol, 2-propanol, mixtures of 2-propanol with water and mixtures of methanol with water.

The process of this invention is typically performed as follows. The amine, the 2,2,6,6-tetraalkyl-4-piperidone, reaction medium and palladium catalyst are all charged to the reactor, which is generally a pressure vessel.

The equivalent ratio of piperidone to amine is preferably within the range of from 1:1 to 1.2:1.

The ratio of reagents to solvent (i.e., reaction medium) is not critical, and typically solvent will comprise between about 5 and about 80 weight percent of the entire reaction mixture.

As is well known to those skilled in the art, for batch reactions the catalyst concentration may vary greatly depending on factors such as reaction temperature, reaction pressure and desired cycle time.

Once the reaction mixture has been introduced to the reaction vessel, the vessel is typically pressurized with hydrogen and, generally, is heated to reaction temperature. The reaction temperature may range between about 15° C. and about 100° C., is preferably between about 45° C. and about 90° C., and is most preferably between about 60° C. and about 85° C. Reaction pressure may range from about 15 to about 2,000 psi, and is preferably between about 50 and 900 psi. Most preferably, the reaction is conducted at between about 100 and about 750 psi.

The reaction time will vary in accordance with factors such as reaction batch size, reaction temperature, reaction pressure, the particular reactants selected and the like. If desired, the progress of the reaction may be followed by monitoring the hydrogen absorption.

Once the reaction has proceeded to the desired extent, the reactor is typically cooled and depressurized. Recovery of the product is typically carried out by first filtering off catalyst, then removing solvent and impurities, including unreacted starting ingredients, from the product by distillation.

By making modifications readily apparent to those skilled in the art, the process of this invention may be carried out in a batch or continuous manner.

EXAMPLES

The following Examples are intended to further illustrate the process of this invention and are not intended to limit the scope of this invention in any manner.

EXAMPLES 1–3 AND COMPARATIVE EXPERIMENT A

To a one-gallon autoclave was added 456.4 grams (2.94 moles) of 2,2,6,6-tetramethyl-4-piperidone, 162.7 grams (1.40 moles) of hexamethylenediamine, 770 ml of the solvent indicated in Table I below, and 28.0 grams of a 5% metal catalyst (palladium in Example 1–3; platinum in comparative Experiment A) on carbon. The autoclave was pressurized with hydrogen. After heating to 80° C., pressure was maintained at 100–200 psig. The reaction was continued for about 1 hour after hydrogen absorption had apparently ceased (i.e., for the times listed in Table I below).

The reactor was cooled to room temperature and the reaction product removed from the reactor. The catalyst was removed from the product by filtration, and the volatiles removed under reduced pressure. The product was analyzed by gas liquid chromatography. The results of such analysis are listed in Table I below.

TABLE I

| | | Low Pressure Process (100–200 psig) | | | |
|---|---|---|---|---|---|
| Example or Comparative Experiment | Reaction Catalyst | Medium | Time at 80° C. (hours) Total | Reaction[a] | Mole % Bis-Product[b] |
| 1 | Palladium | 2-propanol | 5.0 | 3.5 | 97 |
| 2 | Palladium | water | 6.2 | 5.2 | 96 |
| 3 | Palladium | 91% 2-propanol[c] 9% water | 4.6 | 3.5 | 97 |
| A | Platinum | water | 5.3 | 4.3 | 90 |

[a] time at 80° C. during apparent hydrogen absorption.
[b] bis product = N,N'—bis(2,2,6,6-tetramethyl-4-piperidyl)hexamethylenediamine
[c] percent by volume The above results demonstrate the unexpectedly higher yields obtained by the use of a palladium catalyst relative to a platinum catalyst at lower pressures.

EXAMPLES 4 AND 5 AND COMPARATIVE EXPERIMENTS B AND C

To a one liter autoclave was charged 34.8 grams (0.30 mole) of hexamethylenediamine (HMDA), 97.65 grams (0.63 mole) of 2,2,6,6-tetramethyl-4-piperidone (TAA), 120 ml of the reaction medium listed in Table II, and 1.5 grams of a 5% metal (of the type listed in Table II) on carbon catalyst. The autoclave was pressurized with hydrogen. After heating to 80° C., pressure was maintained at 600–800 psig.

The reaction products were concentrated on a rotary evaporator at 95° C. and 30 mm Hg. The products were analyzed by quantitative gas liquid chromatography. The results of such analyses are summarized in Table II below.

TABLE II
HIGH PRESSURE PALLADIUM CATALYSIS

| Example No. | Catalyst | Solvent | Time, hr. | bis[a] | mono[b] | TAA[c] | Alcohol[d] | HMDA |
|---|---|---|---|---|---|---|---|---|
| 4 | Pd | Water | 6.7 | 68 | 10 | 0.16 | 0.07 | N.D.[e] |
| 5 | Pd | Methanol | 5.0 | 88 | 0.12 | 3.5 | N.D. | N.D. |
| B | Pt | Water | 2.4 | 89 | 3.1 | 0.43 | 3.2 | N.D. |
| C | Pt | Methanol | 4.8 | 93 | 0.47 | 2.9 | 0.57 | N.D. |

[a]N,N′—bis(2,2,6,6-tetramethyl-4-piperidyl)hexamethylenediamine.
[b]N—(2,2,6,6-tetramethyl-4-piperidyl)hexamethylenediamine.
[c]2,2,6,6-tetramethyl-4-piperidone.
[d]2,2,6,6-tetramethyl-4-piperidinol; yield based on starting 2,2,6,6-tetramethyl-4-piperidone.
[e]None detected.

The above data indicate that the process of this invention, employing a palladium catalyst, will produce much smaller amounts of 2,2,6,6-tetramethyl-4-piperidinol—an undesirable, unrecyclable byproduct—than will identical processes employing platinum as a catalyst. It is to be noted that if bis-product only is desired, the mono-substituted product and the starting materials (TAA and HMDA) may all be reprocessed.

What is claimed is:

1. A process for producing compounds of the formula:

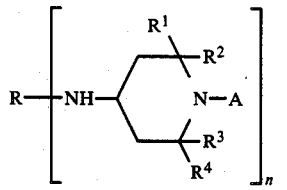

(I)

wherein:
R is $C_1$–$C_{18}$ alkyl, $C_5$–$C_6$ cycloalkyl or $C_7$–$C_9$ aralkyl;
$R^1$, $R^2$, $R^3$ and $R^4$ are the same or different and are $C_1$–$C_8$ alkyl;
A is hydrogen, hydroxy, $C_1$–$C_8$ alkoxy, $C_1$–$C_8$ alkyl, $C_2$–$C_{10}$ alkylcarbonyl or arylcarbonyl; and
n is 1, 2, 3 or 4;
with the proviso that when n is 2, 3 or 4, the $R^1$, $R^2$, $R^3$, $R^4$ and A substituents of the piperidine rings may each independently be different members within the scope of their definitions;
which process comprises reacting an amine of the formula $R(NH_2)_n$, wherein R and n are as defined above, with at least one 2,2,6,6-tetraalkyl-4-piperidone of the formula:

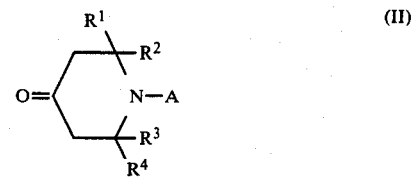

(II)

wherein A, $R^1$, $R^2$, $R^3$ and $R^4$ are as defined above; in the presence of a palladium catalyst employing a reaction medium selected from the group consisting of water and a mixture of water and $C_1$–$C_3$ aliphatic alcohols.

2. The process of claim 1 wherein the reaction is performed at between about 15 and about 2000 psi.
3. The process of claim 2 wherein the reaction is performed at between about 50 and about 900 psi.
4. The process of claim 3 wherein the reaction is performed at between about 100 and about 750 psi.
5. The process of claim 1 wherein the reaction is performed at between about 15° and about 100° C.
6. The process of claim 5 wherein the reaction is performed at between about 45° and about 90° C.
7. The process of claim 6 wherein the reaction is performed at between about 60° and about 85° C.
8. The process of claim 1 wherein $R^1$, $R^2$, $R^3$ and $R^4$ are methyl and A is hydrogen.
9. The process of claim 8 wherein said amine is selected from the group consisting of methylamine, butylamine, dodecylamine, octadecylamine, cyclohexylamine, benzylamine, triethylenediamine, tetraethylenediamine, hexamethylenediamine, 1,12-diaminododecane, dipropylenetriamine, diethylenetriamine, 1,2,6-triaminohexane, and 1,4-diaminocyclohexane.
10. The process of claim 8 wherein said amine is tetraethylenediamine or hexamethylenediamine.
11. The process of claim 1 wherein the reaction medium is water.
12. The process of claim 1 wherein the reaction medium is a mixture of water and alcohol.
13. The process of claim 12 wherein the reaction medium is a mixture of water and 2-propanol.
14. The process of claim 12 wherein the reaction medium is a mixture of ethanol and water.

* * * * *